US 8,513,027 B2

(12) United States Patent
Baxter et al.

(10) Patent No.: US 8,513,027 B2
(45) Date of Patent: Aug. 20, 2013

(54) METHOD OF IDENTIFYING AN INHIBITOR OF THE PROSTANOID EP4 RECEPTOR

(75) Inventors: Gordon S. Baxter, Hertfordshire (GB); Robert A. Coleman, Hertfordshire (GB); Nicholas Tilford, Hertfordshire (GB)

(73) Assignee: Asterand UK Acquisition Limited, London (GB)

( * ) Notice: Subject to any disclaimer, the term of this patent is extended or adjusted under 35 U.S.C. 154(b) by 681 days.

(21) Appl. No.: 11/976,945

(22) Filed: Oct. 30, 2007

(65) Prior Publication Data

US 2008/0247954 A1    Oct. 9, 2008

Related U.S. Application Data

(60) Division of application No. 10/367,906, filed on Feb. 19, 2003, now abandoned, which is a division of application No. 09/534,175, filed on Mar. 24, 2000, now abandoned, which is a continuation-in-part of application No. PCT/GB98/02895, filed on Sep. 25, 1998.

(51) Int. Cl.
*G01N 33/567* (2006.01)

(52) U.S. Cl.
USPC ........................................................ 436/503

(58) Field of Classification Search
USPC ........................................................ 436/503
See application file for complete search history.

(56) References Cited

U.S. PATENT DOCUMENTS

| 4,342,756 | A | 8/1982 | Collington et al. |
| 4,839,384 | A | 6/1989 | Ogletree |
| 5,344,991 | A | 9/1994 | Reitz et al. |
| 5,605,902 | A | 2/1997 | Amer |
| 2003/0158240 | A1 | 8/2003 | Baxter et al. |

FOREIGN PATENT DOCUMENTS

| EP | 0 512 399 A1 | 11/1992 |
| EP | 0 512 400 A1 | 11/1992 |
| EP | 0 539 977 A1 | 5/1993 |
| GB | 2 028 805 | 3/1980 |
| WO | WO 93/09104 | 5/1993 |
| WO | WO 93/13082 | 7/1993 |
| WO | WO 94/25456 | 11/1994 |
| WO | WO 95/12600 | 5/1995 |
| WO | WO 95/17393 | 6/1995 |
| WO | WO 95/24393 | 9/1995 |
| WO | WO 97/03973 | 2/1997 |
| WO | WO 98/55468 | 12/1998 |
| WO | WO 99/47497 | 9/1999 |
| WO | WO 00/18405 | 4/2000 |
| WO | WO 00/21532 | 4/2000 |
| WO | WO 01/10426 A2 | 2/2001 |
| WO | WO 2005/105147 | 11/2005 |

OTHER PUBLICATIONS

Mukhopadhyay P, Geoghegan TE, Patil RV, Bhattacherjee P, and Paterson CA, "Detection of EP2, EP4, and FP receptors in human ciliary epithelial and ciliary muscle cells," Biochemical Pharmacology, May 1997, 53(9), 1249-1255.*
Steele VE, Boone CW, Lubet RA, Crowell JA, Holmes CA, Sigman CC, and Kelloff GJ, "Preclinical drug development paradigms for chemopreventives," Hematology/Oncology Clinics of North America, Oct. 1998, 12(5), 943-961 (abstract provided).*
Walch L, Labat C, Gascard JP, de Montpreville V, Brink C, and Norel X, "Prostanoid receptors involved in the relaxation of human pulmonary vessels," British Journal of Pharmacology, Feb. 1999, 126(4), 859-866.*
Coleman RA, Smith WL,and Narumiya S, "International Union of Pharmacology classification of prostanoid receptors: properties, distribution, and structure of the receptors and their subtypes," Pharmacological Reviews, Jun. 1994, 46(2), 205-229.*
Kiriyama M, Ushikubi F, Kobayashi T, Hirata M, Sugimoto Y, are Narumiya S, "Ligand binding specificities of the eight types and subtypes of the mouse prostanoid receptors expressed in Chinese hamster ovary cells," British Journal of Pharmacology, Sep. 1997, 122(2), 217-224.*
Lydford SJ, McKechnie KC, and Dougall IG, "Pharmacological studies on prostanoid receptors in the rabbit isolated saphenous vein: a comparison with the rabbit isolated ear artery," British Journal of Pharmacology, Jan. 1996, 117(1), 13-20.*
Ebersberger A, Averbeck B, Messlinger K, and Reeh PW, "Release of substance P, calcitonin gene-related peptide and prostaglandin E2 from rat dura mater encephali following electrical and chemical stimulation in vitro," Neuroscience, Mar. 1999, 89(3), 901-907.*

(Continued)

*Primary Examiner* — Paul Zarek
(74) *Attorney, Agent, or Firm* — Nixon & Vanderhye P.C.

(57) ABSTRACT

The present invention provides for the treatment of primary headache disorders, particularly migraine, using antagonists of the $EP_4$ receptor for prostaglandin E2. Particular $EP_4$ receptor antagonists include azole compounds of formula (I):

wherein $R^1$ is a group such as lower alkyl substituted with carboxy; $R^2$ is hydrogen or lower alkyl, $R^3$ and $R^4$ are aryl optionally substituted with halogen,
Q is $$-A^1-\!\!\!\bigcirc\!\!\!_{A^2}\!\!\!-A^3-$$

in which $-A^1-$ is a single bond or lower alkylene, is a cyclo group,
$-A^3-$ is a single bond or lower alkylene, and X is O, NH or S; or a salt or its solvate thereof.

8 Claims, 6 Drawing Sheets

(56) References Cited

OTHER PUBLICATIONS

Thomsen LL and Olesen J, "The autonomic nervous system and the regulation of arterial tone in migraine," Clinical Autonomic Research, Oct. 1995, 5(5), 243-250.*
An et al., Biochem. Biophys. Res. Commun., 1993, 197; 263-270.
Boie et al., (1995) "Molecular Cloning and Characterization of the Human Prostanoid DP Receptor", J. Biol. Chem. 270 (32), 18910-18916.
Boie et al., (1994) "Cloning and Expression of a cDNA for the Human Prostanoid IP Receptor", J. Biol. Chem. 269 (16), 12173-12178.
Carlson et al., (1986) "Clinical and Metabolic Effects of Different Doses of Prostaglandin $E_1$ in Man", Acta Med. Scand. 183, 423.
Coleman, R. A., "Prostanoid Receptors, Classification, Characterisation and Therapeutic Relevance", in *Eicosanoids: From Biotechnology to Therapeutic Applications,* eds., Folco, Samuelsson, Maclouf & Velo., 1996, Plenum Press, New York, pp. 137-154.
Coleman, et al., (1995) "$EP_4$-Receptors and Cyclic AMP in Pig Venous Smooth Muscle: Evidence with Agonists and the $EP_4$-Antagonist, AH22921", *Advances in Prostaglandin, Tromboxane and Leukotriene Research,* ed. Samuelson et al. Raven Press, Ltd. NY 1995, pp. 241-246.
Coleman et al., (1994) "A Novel Inhibitory Prostanoid Receptor in Piglet Saphenous Vein", Prostaglandins, 47 151-168.
Funk et al., (1993) "Cloning and Expression of a cDNA for the Human Prostaglandin E Receptor EP1 Subtype", J. Biol. Chem. 268, (35) 26767-26772.
Hansen, P. (1994) Pharmacol. Toxicol. 75, Suppl. II, 81-82.
Hirata et al., (1991) "Cloning and Expression of the Human Thromboxan A2 Receptor", Naure 349, 617-620.
Honda et al., "Cloning and Expression of a cDNA for Mouse Prostaglandin E Receptor $EP_2$ Subtype", J. Biol. Chem., 1993, 268 (11) 7759-7762.
Humphrey et al., "The Vasoconstrictor Action of Sumatriptan on Human Dura Mater" in *Serotonin: Molecular Biology, Receptors and Functional Effects,* ed. Fozard, J. and Saxena, P.R., Birkhauser Verlag, Basel, (1991) pp. 421-429.
Karachalios et al., "Treatment of Acute Migraine Attack with Diclofenac Sodium: A Double-Blind Study", (1992) Headache 21, 190.
Nattero et al., "Relevance of Prostaglandins inTrue Menstrual Migraine", (1989) Headache 29, 232-237.
Tuca et al., "Increase in $PGE_2$ and $TXA_2$ in the Saliva of Common Migraine Patients. Action of Calcium Channel Blockers", (1989) Headache 29, 498-501.
Parsons et al., "Effects of Prostanoids on Human and Rabbit Basilar Arteries Precontracted In Vitro", Cephalalgia (1989) 9; 165-171.
Peatfield et al., "The Effect of Infused Prostacyclin in Migraine and Cluster Headache", (1981) Headache 21, 190-195.
Regan et al., "Cloning of a Novel Human Prostaglandin Receptor with Characterisatics of the Pharmacologically Defined $EP_2$ Subtype", (1994) Mol. Pharmacol., 46, 213-220.
Regan et al., (1994) Molecular Cloning and Expression of Human $EP_3$ Receptors: Evidence of Three Variants with Differing Carboxyl Termini, Br. J. Pharmacol. 112, 377-3385.
Peatfield et al., "Exacerbation of Migraine by Treatment With Lithium", (1981) Headache, 21: 140-142.
Coleman et al, "A novel inhibitory prostanoid receptor in piglet saphenous vein", Prostaglandins 1994:47, Feb., pp. 151-168; XP-000971160.
Vapaatalo, "Tolfenamic Acid and Migraine—Aspects of Prostaglandins and Leukotrienes", Pharmacology & Toxicology, 1994, 75. Suppl. H. 76 80; XP-000974399.
Kohl, Kopfschmerz durch Arzneimittal; Med. Mo. Pharm. 8. Jahrgang; Heft 1; 1985; XP-000974353.
"Selective Tungsten Nitride Formation", IBM Technical Disclosure Bulletin; vol. 31, No. 2, Jul. 1988, pp. 366-368.
Vardi et al, "Prostaglandin—$E_2$ Levels in the Saliva of Common Women", Headache, Mar. 1983, pp. 59-61.
Parsons et al, "Effects of prostanoids on human and rabbit basilar arteries precontracted in vitro", Cephalalgia, 9 (1989), pp. 165-171; XP-002086056.
Lydford et al, "Characterization of the prostaglandin $E_2$ sensitive (EP)-receptor in the rat isolated trachea", Br. J. Pharmacol. (1994), 112, 133-136.
Tuca et al, "Increase in $PGE_2$ and $TXAS_2$ in the Saliva of Common Migraine Patients, Action of Calcium Channel Blockers", Headache, Sep. 1989, pp. 498-501.
Nattero et al, "Relevance of Prostaglandins in True Menstrual Migraine", Headache, Apr. 1989, pp. 232-239.
Puig-Parellada et al, "Plasma and Saliva Levels of $PGI_2$ and $TXA_2$ in the Headache-Free Period of Classical Migraine Patients. The Effects of Nicardipine", Headache, Mar. 1991, pp. 156-159.
Posner, Disorders of Sensation, Cecil Textbook of Medicine, $20^{th}$ Ed., vol. 2, pp. 2030-2038 (1996).
Machwate et al, Molecular Pharmacology, 2001, vol. 60, No. 1, pp. 36-41.
Abramovitz et al, Biochimica et Biophysica Acta 1483, 2000, pp. 285-293.
*General Electric Company v. Walbash Appliance Corporation* 37 USPQ 466, 469 (US 1938).
*University of Rochester v. G. D. Searle & Co.,* 69 USPQ2d 1886 (CAFC 2004).
*University of California v. Eli Lilly and Co.,* 43 USPQ2d 1398, 1406 (CAFC 1997).
DeBonon et al, "Effect of the specific thromboxane receptor blocking drug AH23848 in patients with angina pectoris", Br. Heart J., 1986:56(6):509-517, abstract.
DeBonon et al, "Effect of the specific thromboxane receptor blocking drug AH23848 in patients with angina pectoris", Br. Heart J., 1986:56(6):509-517.
Tanaka et al, "Molecular Biology of Prostanoid Receptors", Gene & Medicine ("Idenshi-Igaku"), 1998, vol. 2, No. 2, pp. 241-245 (in Japanese).
Coleman et al, "A novel inhibitory prostanoid receptor in piglet saphenous vein", Prostaglandins 1994:47, pp. 151-168.
Araki, "Vascular headache (except for migraine)", Clinical Work and Research ("Rinsho to Kenkyu"), 1991, vol. 68, No. 6, pp. 1615-1619 (in Japanese).
Yamada et al, "Headache and cervical pain", Clinical Work and Research ("Rinsho to Kenkyu"), 1998, vol. 75, No. 7, pp. 1504-1506 (in Japanese).
English translation of Notice of Reasons for Rejection received in connection with copending Patent Application No. JP 2000-571923 mailed Oct. 17, 2008 and describing the reasons for citing Tanaka et al, Araki et al and Yamada et al (see comments on Refs. 1, 3 and 4).
Office Action dated Mar. 17, 2009, issued in corresponding Canadian Patent Application No. 2,402,099.
Wright et al, "Characterization of the recombinant human prostanoid DP receptor and identification of L-644,698, a novel selective DP agonist", British Journal of Pharmacology (1998) 123, 1317-1324.
Maubach, et al, "BGC20-1531, a novel, potent and selective prostanoid EP4 receptor antagonist: a putative new treatment for migraine headache", B. J. Pharmacol. (2009), 156, 316-327.
Japanese Patent Office, Office Action dated Apr. 27, 2010, issued in corresponding Japanese Patent Application No. 2001-570263 (Japanese and English text).
Pradalier, "NSAIDs", Cephalalgia 1999; 19:199-200.
Marin, "Pharmacology Update: Pharmacologic Management of Migraine", Journal of the American Academy of Nurse Practitioners, Sep. 1998, vol. 10, No. 9, pp. 407-412.
Bhattacharya et al, "Localization of Functional Prostaglandin $E_2$ Receptors $EP_3$ and $EP_4$ in the Nuclear Envelope", The Journal of Biological Chemistry, 1999, vol. 274, No. 22, pp. 15719-15724.
JP 9-506894 (Jul. 1997) (Japanese text) counterpart WO 95/17393 Jan. 26, 2009.
JP 2003-506404 (Feb. 2003) (Japanese text) (WO 01/10426 Jan. 26, 2009).

* cited by examiner

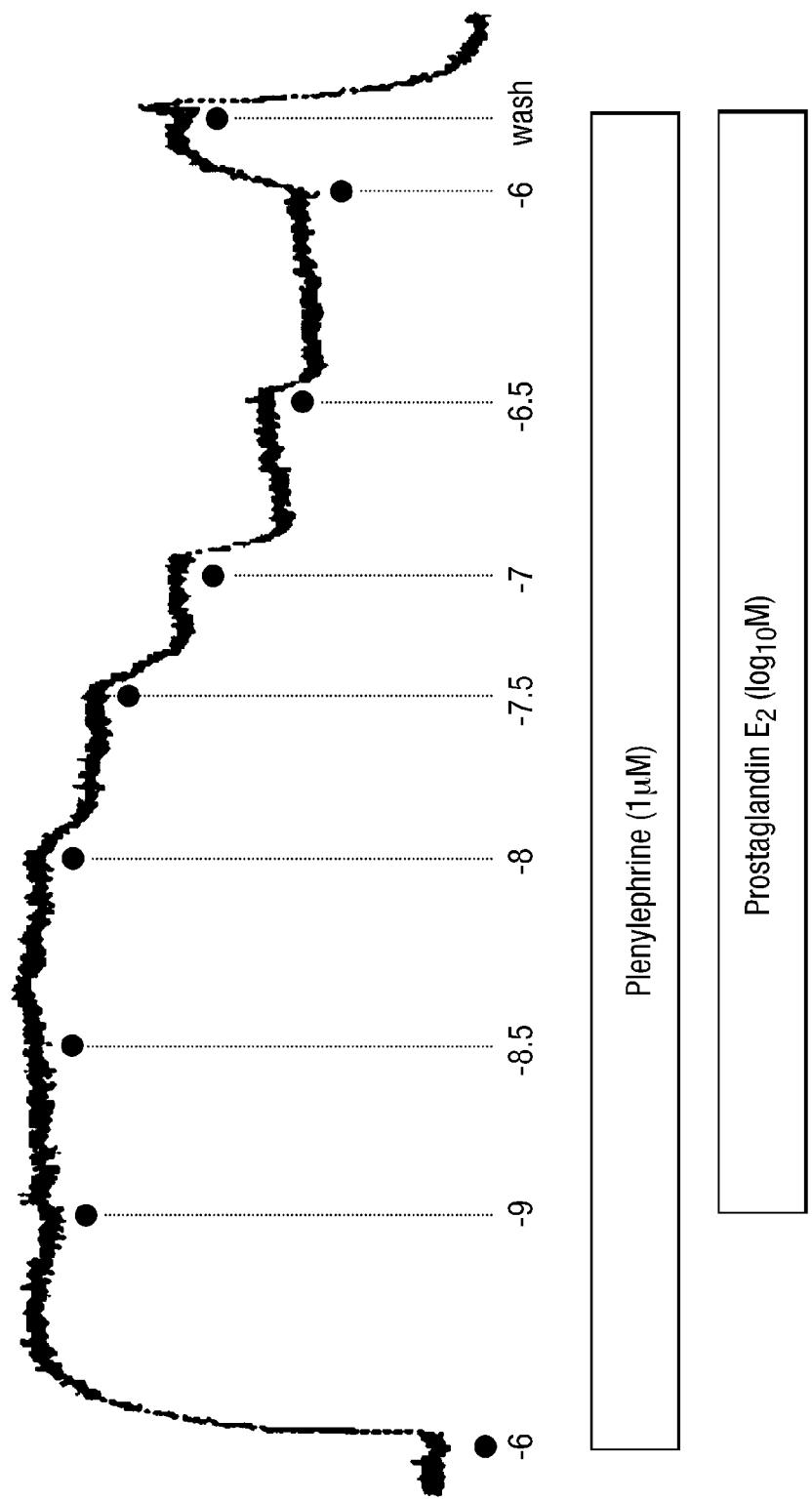

METHOD OF IDENTIFYING AN INHIBITOR OF THE PROSTANOID EP4 RECEPTOR

This application is a divisional of application Ser. No. 10/367,906, filed Feb. 19, 2003 (abandoned), which is a divisional of application Ser. No. 09/534,175, filed Mar. 24, 2000 (abandoned), which is a continuation-in-part of PCT/GB98/02895, filed Sep. 25, 1998, which designated the U.S., the entire contents of each of which are hereby incorporated by reference in this application

FIELD OF THE INVENTION

The present invention relates to a method of treatment of primary headache disorders and drug-induced headaches in humans and other mammals and to the use of compounds in the preparation of a medicament for the treatment of primary headache disorders and drug-induced headaches.

BACKGROUND TO THE INVENTION

There is a widely held view that the pain of migraine headache originates from abnormally distended blood vessels in the cerebral vasculature. Dilatation in cerebral blood vessels, would cause local pressure resulting in the activation of local sensory pathways and pain. This can be the case also for the other aforementioned primary headache disorders and certain drug-induced headaches.

Many drugs are used to treat primary headache disorders such as migraine, including NSAIDs, ergot alkaloids, and several compounds that interact with different subtypes of 5-hydroxytryptamine (5-HT) receptors either as agonists (e.g. sumatriptan) or antagonists (e.g. ketanserin). However, of the drugs that interact with 5-HT receptors only the class of compounds described as $5\text{-HT}_{1D}$ receptor agonists, of which sumatriptan is an example, will relieve an established headache. $5\text{-HT}_{1D}$ receptor agonists are well known to cause vasoconstriction in the cerebral vasculature which supports the vasodilatation theory [Humphrey, P. P. A., Feniuk, W., Motevalian, M., Parsons A. A. and Whalley, E. T., 'The vasoconstrictor action of sumatriptan on human dura mater in 'Serotonin: Molecular Biology, Receptors and Functional Effects' ed. Fozard, J. and Saxena, P. R., Birkhauser Verlag, Basel, 1991].

Exogenous administration of the potent vasodilator E-series, but not I-series, prostanoids to migraineurs is known to induce migraine-like symptoms [Carlson, L. A., Ekelund, L. G. and Oro, L. (1986) Acta Med. Scand. 183, 423; Peatfield, R. (1981) Headache 32, 98-100]. In menstrual migraines plasma concentrations of prostaglandin E2 (PGE2) are significantly increased during the pain phase of the migraine attack (Nattero, G, et al, 1989, Headache 29; 232-237). Similarly, increased levels of $PGE_2$ have been found in saliva of common migraine patients during migraine attacks (Obach Tuca, J, et al, 1989, Headache, 29; 498-501).

This evidence, together with the effectiveness of NSAIDS (which act by inhibiting the biosynthesis of prostanoids) in both preventing or relieving a migraine attack [Karachalios, G. N., Fotiadou, A., Chrisikos, N., Karabetsos, A. and Kehagoiglou (1992) Headache 21, 190; Hansen, P. (1994) Pharmacol. Toxicol. 75, Suppl. 2, 81-82] supports the involvement of prostanoids in the aetiology of the disease. The precise role of prostanoids is unclear but could involve a combination of local vasodilator, inflammatory, and/or hyperalgesic actions. The prostanoid most often associated with such actions is $PGE_2$.

Thromboxane $A_2$ ($TXA_2$), an active metabolite of arachidonic acid in human platelets, is a potent constrictor of vascular smooth muscle and aggregator of platelets. The compounds AH22191 and AH23848 (see below) and related compounds antagonise the actions of $TXA_2$ and therefore inhibit platelet aggregation and bronchoconstriction. Hence these compounds have been claimed for use in the treatment of asthma and as anti-thrombotic agents in cardiovascular disorders. GB Patent 2,028,805 and U.S. Pat. No. 4,342,756 describe AH22921 and AH23848, respectively. These compounds have the following structures:

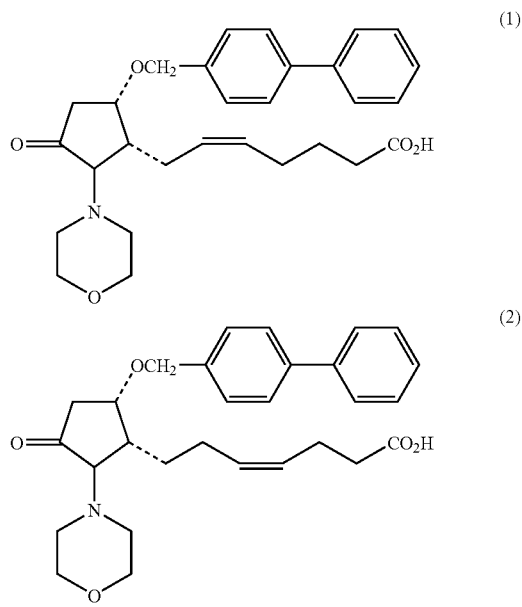

Additionally, both AH22921 and AH23848 have also been shown to be weak antagonists of $PGE_2$-induced relaxation of piglet saphenous vein ($pA_2$ values 5.3 and 5.4, respectively) through blockade of $EP_4$ receptors [Coleman, R. A., Grix, S. P., Head, S. A., Louttit, J. B., Mallett, A. and Sheldrick, R. L. G. (1994) Prostaglandins 47, 151-168; Coleman, R. A., Mallett, A. and Sheldrick, R. L. G. (1995) Advances in Prostaglandin, Thromboxane and Leukotriene Research, 23, 241-246] but have no effect on other EP receptor subtypes $EP_1$, $EP_2$ and $EP_3$.

A large number of $PGE_2$ antagonists are known. These include oxazole derivatives, such as those disclosed in WO98/55468, dibenzoxazepine derivatives such as those of EP-A-0512399, EP-A-0512400, EP-A-0539977, WO93/09104, WO93/13082, WO94/25456 and WO95/12600, 1,2-diarylcyclopentenyl compounds such as those of U.S. Pat. No. 5,344,991, and carboxylic acids and acyl-sulphonamides such as those of WO99/47497, the disclosures of all of which are incorporated herein by reference.

DISCLOSURE OF THE INVENTION

We have examined the action of a number of prostanoids on human isolated cerebral blood vessels and made the unexpected discovery that $PGE_2$ has a complex action on these vessels whereas the other vasodilator prostanoids, $PGD_2$ and $PGF_{2\alpha}$, produce no effects. $PGE_2$ can cause constriction of larger vessels (>than 1 mm diameter), but more significantly we believe, in the context of pain associated with migraine, it has surprisingly been found that it causes a potent concentration-related relaxation of smaller cerebral vessels (<1 mm diameter). By studying a variety of pharmacologically active agents this relaxant effect was found to be mediated by prostanoid $EP_4$ receptors. Further experiments carried out in human coronary and pulmonary arteries have shown that $PGE_2$ lacks this dilatory effect in these tissues. Therefore, and in contrast with current anti-migraine drug treatments, it is not expected that $EP_4$ receptor antagonists will cause significant cardiovascular problems.

Thus our findings described herein are consistent with the novel theory that relaxation of small cerebral arteries by $PGE_2$ is mediated via $EP_4$ receptors. Thus $EP_4$ receptor antagonists, particularly selective $EP_4$ antagonists, are useful in preventing the relaxation of such arteries.

We therefore believe this unexpected action of $PGE_2$ could account for the pain in migraine. Preventing increased blood flow to these small cerebral arteries has positive implications in the treatment of migraine and drug induced headaches. Thus an $EP_4$ receptor antagonist, particularly a selective $EP_4$ receptor antagonist, may provide a novel and effective anti-migraine agent with advantages over existing therapies, especially NSAIDS. As well as less side effect liability, an $EP_4$ receptor antagonist should exhibit greater efficacy than an NSAID because an NSAID would eliminate both the detrimental vasodilator and beneficial vasoconstrictor effects on cerebral vasculature caused by endogenous prostaglandins. In contrast, an $EP_4$ receptor antagonist should only inhibit the detrimental vasodilator effect.

Thus in a first aspect, the invention relates to a new medical use for compounds which act as antagonists at prostanoid $EP_4$ receptors and pharmaceutical compositions containing them. In particular, the invention relates to the use of such $EP_4$ receptor antagonists in a method of treatment of primary headache disorders such as migraine, which method comprises administering an effective amount of an $EP_4$ receptor antagonist or a pharmaceutically acceptable salt and/or solvate thereof.

There is also provided, according to a further aspect, the use of an $EP_4$ receptor antagonist in the preparation of a medicament for use in the treatment of primary headache disorders or drug-induced headaches.

The surprising finding that $EP_4$ receptor-mediated dilatation of cereberal blood vessels is a major pathway in the induction of primary headache disorders provides novel assay methods for the identification and validation of therapeutic agents.

Accordingly, the present invention provides an assay method for an agent for the treatment of a primary headache disorder or drug-induced headache, which assay comprises:
(a) providing an $EP_4$ receptor;
(b) bringing a potential agent for said treatment into contact with said receptor;
(c) determining whether said agent is capable of interacting with said $EP_4$ receptor; and
(d) selecting an agent which so interacts as an agent for the treatment of primary headache disorder or drug-induced headache.

DESCRIPTION OF THE DRAWINGS

FIG. 1 shows concentration-related relaxation of pre-contracted cerebral blood vessels by $PGE_2$.

DETAILED DESCRIPTION OF THE INVENTION

Figure 2A:
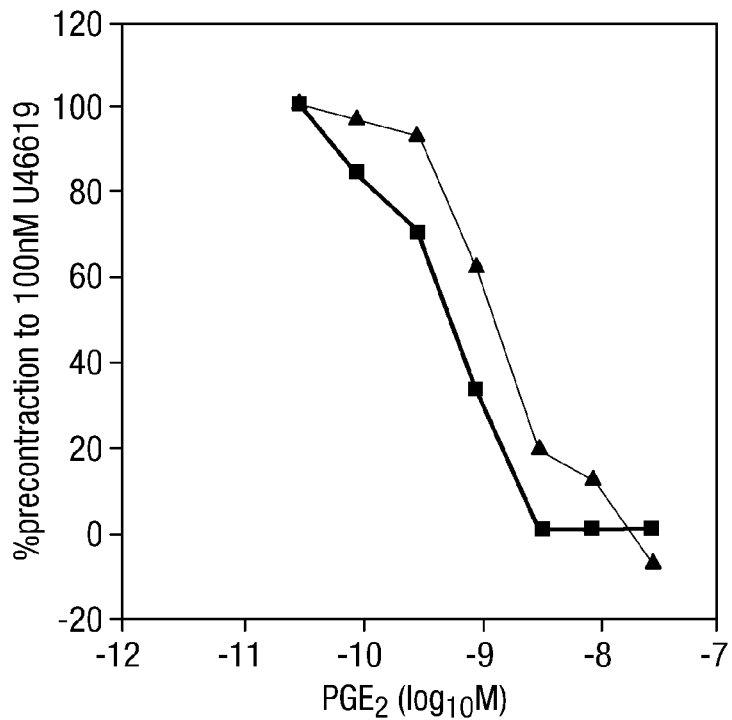
FIG. 2 shows concentration-related relaxation by $PGE_2$ of cerebral blood vessels pre-contracted by (A) U46619, and (B) and (C), 5-HT.

Disorders to be Treated.

As used herein, the term "primary headache disorder" includes migraine, tension-type headache, cluster headache, analgesic rebound headache, chronic paroxysmal hemicrania and headache associated with vascular disorders.

In a preferred aspect, the invention relates to the treatment of, and assays for agents for treating, migraine. Migraine attacks are classified as migraine with—or migraine without aura. Although diagnostic criteria are somewhat different the (drug) treatment is the same. Migraine without aura is described as: idiopathic, recurring headache disorder, manifesting in attacks lasting 4-72 hours, in which headaches are typically unilateral, throbbing, of moderate to severe intensity, aggravated by routine physical activity, and accompanied by nausea and intolerance to brightness and noise. Migraine with aura is described as: idiopathic, recurring disorder manifesting with attacks of neurological symptoms unequivocally localisable to cerebral cortex or brain stem, usually developing over 5-20 minutes and lasting less than 60 minutes, and followed or accompanied by migraine headache and its associated features.

Drug-induced headache, particularly ergotamine-induced headache, is a common problem in migraine treatment. Some case reports suggest that even the new serotonergic antimigraine drugs such as sumatriptan can lead to overuse and subsequent drug-induced headache.

"$EP_4$ Receptor Antagonist".

For the avoidance of doubt, in the context of this invention, an $EP_4$ receptor antagonist is any compound, agent or mixture showing antagonist activity at $EP_4$ receptors, including and especially antagonist activity against $PGE_2$ induced relaxation of human isolated cerebral blood vessels.

In any of the above aspects of the invention the $EP_4$ receptor antagonist is a chemical entity that blocks the activity of $PGE_2$ at the (human) $EP_4$ receptor or better, any chemical entity that competes with $PGE_2$, or any other $EP_4$ receptor ligand, for the $EP_4$ receptor binding site (preferably in a competitive manner) and does not exert any activity itself at the $EP_4$ receptor.

In one aspect the invention provides for the use of AH22921(1) or AH23848(2) or pharmaceutically acceptable salts and/or solvates thereof for the manufacture of a medicament for the use in the treatment of primary headache disorders or drug induced headaches.

In another aspect, the invention provides the use for the manufacture of a medicament for use in the treatment of primary headache disorders or drug induced headaches, of an oxazole compound of formula (I):

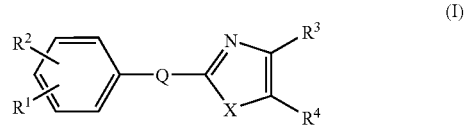

(I)

wherein $R^1$ is lower alkyl substituted with hydroxy, protected carboxy or carboxy; carboxy; protected carboxy; carbamyol; a heterocyclic group; cyano; hydroxy; halo(lower)

alkylsulfonyloxy; lower alkoxy optionally substituted with hydroxy or carbamoyl; aryl substituted with carboxy, protected carboxy, carbamoyl or a heterocyclic group; or amino optionally substituted with protected carboxy or lower alkylsulfonyl, $R^2$ is hydrogen or lower alkyl,
$R^3$ is aryl optionally substituted with halogen,
$R^4$ is aryl optionally substituted with halogen,
Q is

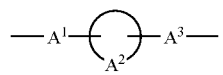

in which -$A^1$- is a single bond or lower alkylene,

is cyclo($C_5$-$C_9$)alkane, bicyclo($C_6$-$C_9$)alkane or bicycle($C_5$-$C_9$)alkane and -$A^3$- is a single bond or lower alkylene, and X is O, NH or S;
or a salt or its solvate thereof.

The compounds of formula (I) may contain one or more asymmetric centres and thus they can exist as enantiomers or diastereoisomers. Furthermore certain compounds of formula (I) which contain alkenyl groups may exist as cis- or trans-isomers. In each instance, mixtures and separate individual isomers may be prepared.

The compounds of the formula (I) may also exist in tautomeric forms and the invention includes both mixtures and separate individual tautomers.

The compound of the formula (I) and its salt can be in a form of a solvate, which is included within the scope of the present invention. The solvate preferably include a hydrate and an ethanolate.

The term "lower" is intended to mean 1 to 6 carbon atom(s), unless otherwise indicated.

Suitable "lower alkyl" and lower alkyl moiety in the term "halo(lower)alkylsulfonyl" and "lower alkysulfonyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "lower alkylene" may include straight or branched one having 1 to 6 carbon atom(s), such as methylene, ethylene, trimethylene, tetramethylene, pentamethylene and hexamethylene, preferably one having 1 to 3 carbon atoms(s), more preferably methylene.

Suitable "cyclo($C_1$-$C_9$)alkane" may include cyclopropane, cyclopentane, cyclohexane, cycloheptane, cyclooctane, or the like, preferably one having 5 to 7 carbon atoms.

Suitable "cyclo($C_5$-$C_9$)alkene" may include cyclopentene, cyclohexene, cycloheptene, cyclooctene, or the like, preferably one having 5 to 7 carbon atoms.

Suitable "bicyclo($C_5$-$C_9$)alkane" may include bicycloheptane (e.g., bicyclo[2.2.1]heptane, etc.), bicyclooctane (e.g., bicyclo[3.2.1]octane, etc.), or the like.

Suitable "bicyclo($C_6$-$C_9$)alkene" may include bicycloheptene (e.g., bicyclo[2.2.1]hept-2-ene, etc.), bicyclooctene (e.g., bicyclo[3.2.1]oct-2-ene, etc.), or the like.

Suitable "aryl" may include phenyl, lower alkylphenyl (e.g., tolyl, ethylphenyl, propylphenyl, etc.), naphthyl or the like.

Suitable "heterocyclic group" may include one containing at least one hetero atom selected from nitrogen, sulfur and oxygen atom, and may include saturated or unsaturated, monocyclic or polycyclic group, and preferably one may be heterocyclic group such as 3 to 6-membered heteromonocyclic group containing 1 to 4 nitrogen atoms, for example, pyrrolyl, pyrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), or the like, more preferably tetrazolyl.

Suitable "lower alkoxy" may include methoxy, ethoxy propoxy, isopropoxy, butoxy, isobutoxy, t-butoxy, pentyloxy, t-pentyloxy, hexyloxy, or the like, preferably methoxy.

Suitable "protected carboxy" may include esterified carboxy or the like.

Suitable example of the ester moiety of an esterified carboxy may be the ones such as lower alkyl (e.g., methyl, ethyl, propyl, isopropyl, butyl, isobutyl, tert-butyl, pentyl, hexyl, etc.) which may have at least one suitable substituent(s), for example, lower alkanoyloxy(lower)alkyl [e.g., acetoxymethyl, butyryloxymethyl, valeryloxymethyl, pivaloyloxymethyl, etc.], halo(lower)alkyl (e.g., 2-iodoethyl, 2,2,2-trichloroethyl, etc.); lower alkenyl (e.g., vinyl, allyl, etc.); lower alkynyl (e.g., ethynyl, propynyl, etc.); ar(lower)alkyl which may have at least one suitable substituent(s) (e.g., benzyl, 4-methoxybenzyl, 4-nitrobenzyl, phenethyl, trityl, etc.); aryl which may have at least one suitable substituent(s) (e.g., phenyl, tolyl, 4-chlorophenyl, tert-butylphenyl, xylyl, mesityl, cumenyl, etc.); phthalidyl; or the like.

Suitable "halo" group in the term of "halo(lower)alkylsulfonyl" may include fluoro, chloro, bromo, iodo, or the like.

Suitable "halo(lower)alkylsulfonyloxy" may include trifluoromethanesulfonyloxy, or the like.

Preferred embodiments of the azole compounds (I) are as follows:

$R^1$ is lower alkyl substituted with carboxy; carboxy; protected carboxy; carbamoyl; a heterocyclic group; lower alkoxy substituted with carbamoyl; aryl substituted with carboxy, carbamoyl or a heterocyclic group; or amino optionally substituted with lower alkylsulfonyl (more preferably lower alkyl substituted with carboxy; carboxy; carbamoyl; tetrazolyl; lower alkoxy substituted with carbamoyl, aryl substituted with carboxy or carbamoyl), $R^2$ is hydrogen or lower alkyl,
Q is

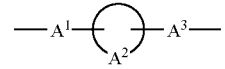

in which -$A^1$- is a single bond or lower alkylene (more preferably methylene),

is cyclo($C_5$-$C_9$)alkene, cyclo($C_3$-$C_9$)alkane or bicyclo($C_6$-$C_9$) alkene, bicyclo($C_5$-$C_9$)alkane (more preferably cyclo ($C_5$-$C_7$)alkene, cyclo($C_5$-$C_7$)alkane, byciclo[2.2.1]heptane or byciclo[2.2.1]heptane), and -$A^3$- is a single bond or lower alkylene (more preferably single bond) and X is O.

A compound of the formula (I) is 3-([2-(4,5-diphenyloxazol-2-yl)-2-cyclohexen-1-yl]methyl)benzoate, or a salt thereof, particularly the sodium salt.

Suitable salts of the compound of formula (I) are pharmaceutically acceptable conventional non-toxic salts and include a metal salt such as an alkali metal salt (e.g. a sodium or potassium salt) and an alkaline earth metal salt (e.g. a calcium or magnesium salt), an ammonium salt, an organic base salt (e.g., a trimethylamine salt, triethylamine salt, pyridine salt, picoline salt or a dicyclohexylamine salt), an organic acid salt (e.g., an acetate, maleate, tartrate, methanesulfonate, benzenesulfonate, formate, toluenesulfonate or trifluoroacetate salt), an inorganic acid salt (e.g., a hydrochloride, hydrobromide sulfate or phosphate), or a salt with an amino acid (e.g., arginine, aspartic acid or glutamic acid).

Compounds of the formula (I), and processes for their production are described in WO98/55468. This citation discloses that these compounds, including salts and solvates thereof, are $EP_4$ receptor antagonists. Although a large number of therapeutic uses of these compounds are described, these do not include the treatment of primary headache disorders, including migraine.

Selective $EP_4$ Receptor Antagonist.

In a preferred embodiment, the $EP_4$ receptor antagonist is a selective $EP_4$ receptor antagonist. By this it is meant that the antagonist has a binding affinity for the $EP_4$ receptor which is at least 10-fold higher than for at least one of the receptors $EP_1$, $EP_2$ and $EP_3$. Preferably the binding is selective with respect to $EP_3$, since we have also found that $PGE_2$ causes contraction of cerebral arteries via interaction with $EP_3$ receptors. More preferably, the $EP_4$ receptor binding is selective with respect to all of $EP_1$, $EP_2$ and $EP_3$.

The binding of an antagonist to the $EP_4$ receptor may be determined by competition against $PGE_2$. For example, the $EP_4$ receptor may be provided as a recombinantly produced receptor expressed in human cell lines. The murine and human $EP_4$ receptors have been cloned (Honda et al J. Biol. Chem., 1993, 268; 7759-7762; and An et al, Biochem. Biophys. Res. Commun., 1993, 197; 263-270), although these were initially characterised in error as $EP_2$ receptors (see review by Coleman, R. A., Prostanoid Receptors, Classification, Characterisation and Therapeutic Relevance, in Eicosanoids: From Biotechnology to Therapeutic Applications, eds. Folco, Samuelsson, Maclouf & Velo., 1996, Plenum Press, New York, pages 137-154), the text of which is also imported herein by reference and forms an integral part of this disclosure.

A method of identifying and quantifying $EP_4$ receptor antagonists is described in the two publications by Coleman, R. A., 1994 and 1995, listed above. The entire text of these publications is hereby imported by reference and forms an integral part of this disclosure and the inventive concepts described.

In one method, $EP_4$ receptor antagonists may be characterised by providing a natural source of the receptors, such as piglet saphenous vein. Sections of vein from freshly killed animals may be cut into rings of 4-5 mm width and suspended in an organ bath in Krebs solution. Changes in vessel tension in response to test compounds may be determined by isometric transducers connected to a suitable recording device. The tissue may be contracted, e.g. with phenyleprine, and the relaxant effect of increasing concentrations of $PGE_2$ determined. The relaxant effect may be determined in the presence or absence of potential antagonists, with a shift in the concentration of $PGE_2$ required to provide an specified degree of relaxation being indicative of an antagonistic effect.

In another method, $EP_4$ receptor antagonists may be characterised using sections of cerebral artery. This is because we have found that this is the predominant $PGE_2$ relaxant receptor in this blood vessel. Sections of cerebral artery are removed from different regions of preparations of human cerebral vasculature containing an intact circle of Willis. Intact rings of this cerebral artery, 2-3 mm in length, are set up under isometric conditions in 10 ml organ baths under an initial tension of 1 g. All tissues are maintained at 37° C. and gassed constantly with 95% $O_2$/5% $CO_2$. Following a 90 min equilibration period all tissues are challenged with phenylephrine (1 μM), to determine tissue viability. Once a stable contraction is obtained, tissues are exposed to a range of prostanoid receptor agonists, in the absence or presence of receptor antagonists, to determine the functional role of prostanoid receptors in maintaining arterial tone.

Combined Therapies.

In a further aspect of the present invention $EP_4$ receptor antagonists may, if desired, be used in combination with one or more other therapeutic agents. The other therapeutic agent(s) may be an agent active against a primary headache disorder, or an agent whose side-effects may induce a primary headache disorder, such as a chemotherapeutic agent. Agents for the treatment of a primary headache disorder include an ergot derivative, for example dihydroergotamine, a $5-HT_2$ receptor antagonist, for example ketanserin, or a $5-HT_{1D}$ receptor agonist, for example sumatriptan, naratriptan or zolmitriptan, a β-blocker for example propranolol, or a non-steroidal anti-inflammatory drug, such as aspirin, paracetamol (acetaminophen) or ibuprofen.

Thus the present invention provides a composition comprising an $EP_4$ receptor antagonist and a second pharmaceutically active ingredient, including any of the ingredients mentioned above. Particular $EP_4$ receptor antagonists include those of formula (I) as defined above, including its preferred embodiments.

A further embodiment of the invention is the combination of an $EP_4$ receptor antagonist with other therapeutic agents used in the treatment of a primary headache disorder such as migraine for example, with an ergot derivative (e.g. dihydroergotamine), a $5-HT_2$ receptor antagonist (e.g. ketanserin), or a $5-HT_{1D}$ receptor agonist (e.g. sumatriptan, naratriptan or zolmitriptan), a β-blocker (e.g. propranolol) or an NSAID including those mentioned above. Particular $EP_4$ receptor antagonists include those of formula (I) as defined above, including its preferred embodiments.

Assay Methods.

In relation to assays of the invention, in a preferred embodiment, the invention provides an assay method for an agent for the treatment of a primary headache disorder or drug-induced headache, which assay comprises:

(a) providing an $EP_4$ receptor;
(b) bringing a potential agent for said treatment into contact with said receptor;
(c) determining whether said agent is capable of interacting with said $EP_4$ receptor; and
(d) selecting an agent which so interacts as an agent for the treatment of primary headache disorder or drug-induced headache.

The mode of interaction of the agent with the $EP_4$ receptor will be determined according to the format of the assay, which may be varied within the routine skill and knowledge of those of skill in the art. For example, in one aspect the assay may simply determine the binding of the agent to the $EP_4$ receptor. There are numerous ways in which such an assay could be performed. For example, the receptor may be provided on a solid support, and the binding of the agent determined in a competitive assay in which the agent, or a competitor (e.g. $PGE_2$ or a known $EP_4$ receptor antagonist) is labelled, so that the displacement of the competitor by the agent may be determined as an indication of binding. Other binding formats, for example in which the receptor is labelled, may be provided within the ordinary skill and knowledge of those in the art.

Alternatively, the assay may be one in which the response of $EP_4$ receptors in a biological system is determined. The receptors may be provided on tissue which naturally expresses these receptors. For example, the receptor may be provided on isolated vasculature, such as cerebral arteries. The vasculature may be isolated from any suitable source, e.g. post-mortem human sources, or animal sources, such as pigs, rats, rabbits and the like. Alternatively, the receptor may be provided by recombinant expression from an $EP_4$ receptor cDNA in a suitable host cell expression system. The biological response to the agent may be determined, e.g. to see if the agent antagonises the response to $PGE_2$ or the like.

In a preferred aspect, the $EP_4$ receptor is provided in step (a) together with at least one other receptor selected from the group of $EP_1$, $EP_2$, $EP_3$ TP, IP and DP receptors. Alternatively, the assay is run in parallel or sequential to (either before or after) with an assay to determine the interaction of the agent to one of these other prostanoid receptors. In this aspect, the determining step may include a comparison of the activity or affinity of the agent against the other EP or other prostanoid receptor types so as to determine whether or not the antagonist is a selective $EP_4$ receptor antagonist. Such selective antagonists are preferred.

In a particularly preferred embodiment, the affinity of the putative $EP_4$ receptor antagonist to the $EP_3$ receptor is determined in the presence of a preparation of $EP_3$ receptors. For example, the affinity of binding of an $EP_4$ receptor antagonist to the $EP_3$ receptor may be determined using a selective radioligand to the $EP_3$ receptor. Preferably, the test selected as an $EP_4$ receptor antagonist will show lower affinity to the $EP_3$ receptor than to the $EP_4$ receptor.

Agents selected by the assays of the invention may then be subject to one or more of the following steps:
(e') testing the agent so selected for safety and/or toxicity in a human or animal subject;
(e'') testing the agent so selected in a human patient for efficacy in treating a primary headache disorder;
(e''') formulating the agent with one or more carriers, diluents or second agents for the treatment of primary headache disorders.

Where other receptors are used in assays according to the invention, these may also be supplied in recombinant form. The cloning of these receptors are described in the following citations, the disclosures of which are incorporated herein by reference.

DP: Boie, Y., Sawyer, N., Slipetz, D. M., Metters, K. M. and Abramovitz, M (1995) Molecular Cloning and characterization of the human prostanoid DP receptor. J. Biol. Chem. 270, 18910-18916.

EP1: Funk, C. D., Furci, L., FitzGerald, G. A., Grygorczyk, R., Rochette, C., Bayne, M., Abramovitz, M., Adam, M. and Metters, K. M. (1993) Cloning and expression of a cDNA for the human prostaglandin E receptor EP1 subtype. J. Biol. Chem. 268, 26767-26772

EP2: Regan, J. W., Bailey, T. J., Pepperl, D. J., Pierce. K. L., Bogardus, A. M., Donello, J. E., Fairbairn, C. E., Kedzie, K. M., Woodward, D. F. and Gil, D. W. (1994) Cloning of a novel human prostaglandin receptor with characteristics of the pharmacologically defined EP2 subtype. Mol. Pharmacol. 40, 213-220.

EP3: Regan, J. W., Bailey, T. J., Donello, J. E., Pierce, K. L., Pepperl, D. J., Zhang, D., Kedzie, K. M., Fairbarin, C. E., Bogardus, A. M., Woodward, D. F. and Gil, D. W. (1994) Molecular cloning and expression of human EP3 receptors: presence of three variants with differing carboxyl termini. Br. J. Pharmacol. 112, 377-385.

TP: Hirata, M., Hayishi, Y., Ushikubi, F., Yokota, Y., Kageyama, R., Nakanishi, S. and Narumiya, S. (1991) Cloning and expression of the human thromboxane A2 receptor. Nature 349, 617-620.

IP: Boie, Y., Rushmore, T. H., Darmon-Goodwin, A., Grygorczyk, R., Slipetz, D. M., Metters, K. M. and Abramovitz, M. (1994) Cloning and expression of a cDNA for the human prostanoid IP receptor. J. Biol. Chem. 269, 12173-12178.

In preferred aspects of this part of the invention, the $EP_4$ receptor is provided together with, or in parallel with, at least one other EP receptor, preferably at least the $EP_3$ receptor. The other receptor(s) may be provided in the various forms (e.g. isolated on a solid support, in tissue on which it occurs naturally or recombinantly) mentioned above. Conveniently, the assay is performed on vasculature which contains the $EP_4$ receptor together with any other desired receptor.

Compounds of the formula (I) as defined above, may be used in assays of the invention in order to select an agent which is a selective $EP_4$ receptor antagonist. Other agents which may be used in performing assays of the invention include other compounds such as $PGE_2$ antagonists described in the patent applications cited above. Further, libraries of small molecules are commercially available and such libraries may be used in assays of the invention.

Formulation and Administration of $EP_4$ Receptor Antagonists.

The $EP_4$ receptor antagonists may be administered as the raw chemical but the active ingredients are preferably presented as a pharmaceutical formulation. Suitable pharmaceutical formulations are described in the above referenced patent specifications.

Thus, the $EP_4$ antagonists may be formulated for oral, buccal, parenteral, topical, depot or rectal administration or in a form suitable for administration by inhalation or insufflation (either through the mouth or nose). Oral and parenteral formulations are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); filters (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxbenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The $EP_4$ antagonists may be formulated for parenteral administration by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The $EP_4$ antagonists may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The $EP_4$ antagonists may also be formulated in rectal compositions such as suppositories or retention enemas, e.g. containing conventional suppository bases such as cocoa butter or other glycerides.

The $EP_4$ antagonists may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the $EP_4$ antagonists may be formulated as solutions for administration via a suitable metered or unit dose device or alternatively as a powder mix with a suitable carrier for administration using a suitable delivery device.

Suitable dose ranges may be calculated by those skilled in the art in light of toxicological data. It will be appreciated that it may be necessary to make routine variations to the dosage, depending on the age and condition of the patient, and the precise dosage will be ultimately at the discretion of the attendant physician or veterinarian. The dosage will also depend on the route of administration and the particular compound selected. A suitable dose range is, for example, 0.01 to 100 mg/kg, such as from 0.01 to about 50 mg/kg bodyweight, 1 to 4 times per day.

The invention is illustrated by the following examples, which shows that small cerebral arteries have $EP_4$ receptors. $PGE_2$ Causes Dilatation of Middle and Anterior Cerebral Arteries In Vitro, Via Interaction with $EP_4$ Receptors.
Materials and Methods.

Sections of cerebral artery were removed from different regions of preparations of human cerebral vasculature containing an intact circle of Willis. Intact rings of this cerebral artery, 2-3 mm in length, were set up under isometric conditions in 10 ml organ baths under an initial tension of 1 g. All tissues were maintained at 37° C. and gassed constantly with 95% $O_2$/5% $CO_2$. Following a 90 min equilibration period all tissues were challenged with phenylephrine (1 µM), to determine tissue viability. Once a stable contraction had been obtained, tissues were exposed to a range of prostanoid receptor agonists, in the absence or presence of receptor antagonists, to determine the functional role of prostanoid receptors in maintaining arterial tone.
Results The effects of prostanoid activation were determined in varying sizes of human cerebral artery. On larger vessels (internal diameter>1 mm), $PGE_2$ generally caused a concentration-related contraction, whereas on smaller vessels (internal diameter<1 mm), it consistently caused potent concentration-related relaxation of pre-contracted cerebral blood vessels. This is shown in FIG. 1, which is a trace showing the relaxant effects of $PGE_2$ on a cerebral blood vessel in an isolated tissue chamber. The isolated vessel has been pre-contracted with phenylephrine and exposed to increasing concentrations of $PGE_2$. Maximum relaxation occurs below $10^{-6}$M and can be maintained until it is washed out.

Figure 2B:
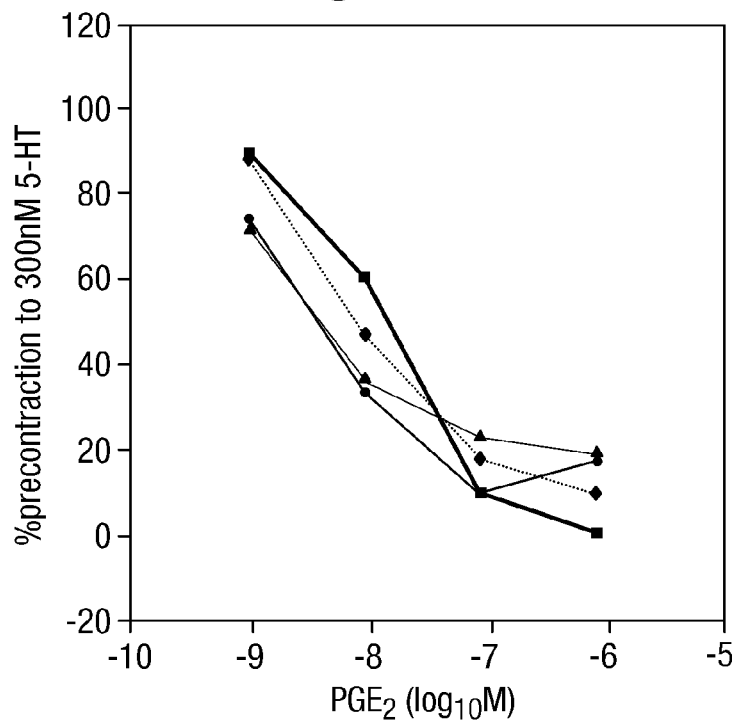
Figure 2C:
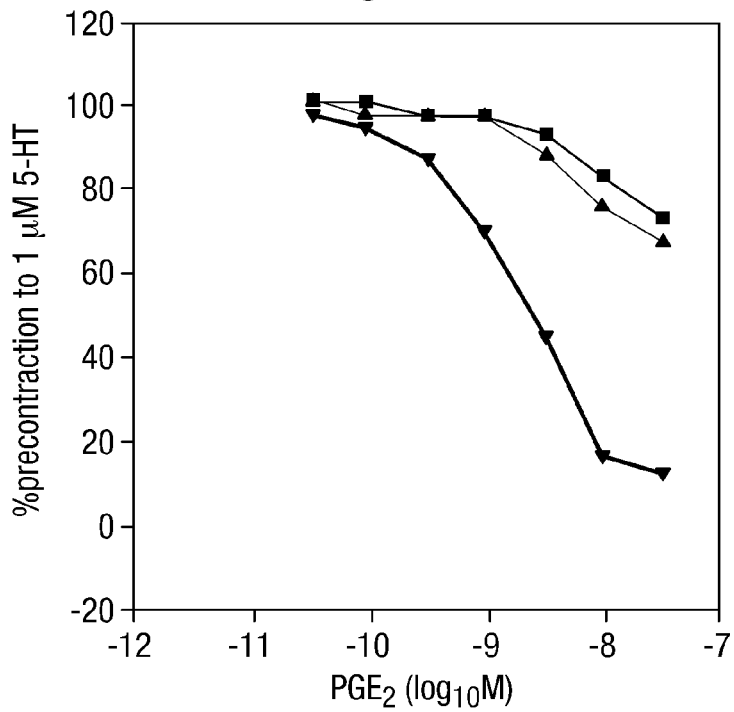

Additionally $PGE_2$ was shown to induce maximal or near maximal relaxation of cerebral artery rings pre-contracted with the TP receptor agonist U46619 (11α,9α-epoxymethano-$PGH_2$), (100 nM) or 5-hydroxytryptamine (5-HT), (300 nM and 1 µM). This is shown in FIG. 2, in which is shown the cumulative concentration-effect curves to the relaxant effects of $PGE_2$ on human cerebral artery rings pre-contracted with: (A) U46619 (100 nM); (B) 5-HT (300 nM) and (C) 5-HT (1 µM). Each curve represents a different tissue.

Figure 3:
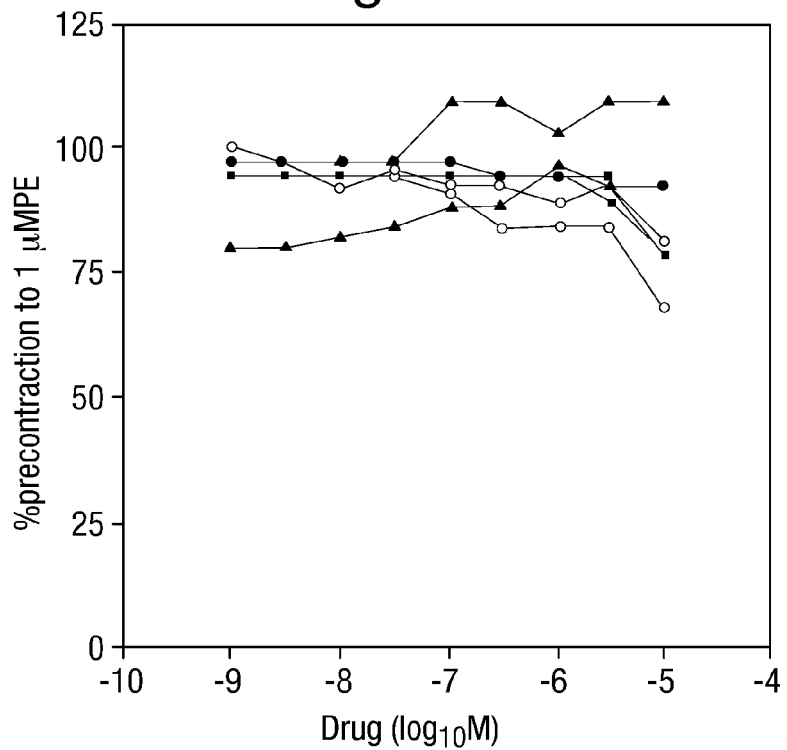
FIG. 3 shows the effect of prostanoids $PGD_2$ and $PGF_{2\alpha}$ on smaller diameter cerebral blood vessels.

On smaller diameter cerebral blood vessels, the closely related prostanoids, $PGD_2$ and $PGF_{2\alpha}$, were found to be without effect, as illustrated in FIG. 3, which shows the cumulative concentration-effect curves to $PGD_2$ (open symbols) and $PGF_{2\alpha}$ (closed symbols) on human cerebral artery rings contracted with phenylephrine (1 µM). GR32191 (4-heptenoic acid, 7-[5-([1,1'-biphenyl]-4-ylmethoxy)-3-hydroxy-2-(1-piperidinyl)-cyclopentyl]-,hydrochloride,[1R[1.alpha.(Z), 2.beta., 3.beta., 5.alpha.]]), (1 µM), was present in bathing solution to block prostanoid TP-receptors. Each curve represents a different tissue.

Figure 4:
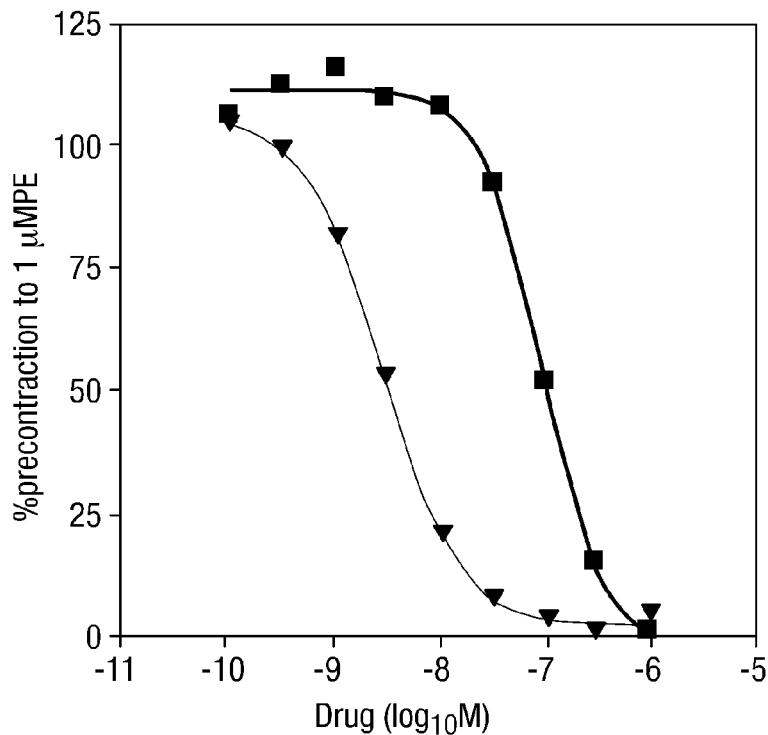
FIG. 4 shows the relaxant response of cerebral blood vessels to iloprost and cicaprost.

The presence of IP receptors on human cerebral artery rings was also investigated. Iloprost and cicaprost induced relaxation in tissues previously contracted with phenylephrine. It was therefore essential that any involvement of IP receptors in mediation of the effects of $PGE_2$ was excluded when assessing antagonist effects at EP receptors. The results of an experiment showing this is set out in FIG. 4, which illustrates the cumulative concentration-effect curves to iloprost (closed squares) and cicaprost (closed triangles) on human cerebral artery rings contracted with phenylephrine (1 µM). GR32191 (1 µM) was present in bathing solution to block prostanoid TP-receptors. However, $PGE_2$ is at least 100-fold less potent at IP receptors compared to iloprost and cicaprost, and therefore relaxation due to IP receptor activation is unlikely to be a major component of $PGE_2$ relaxant response.

Figure 5:
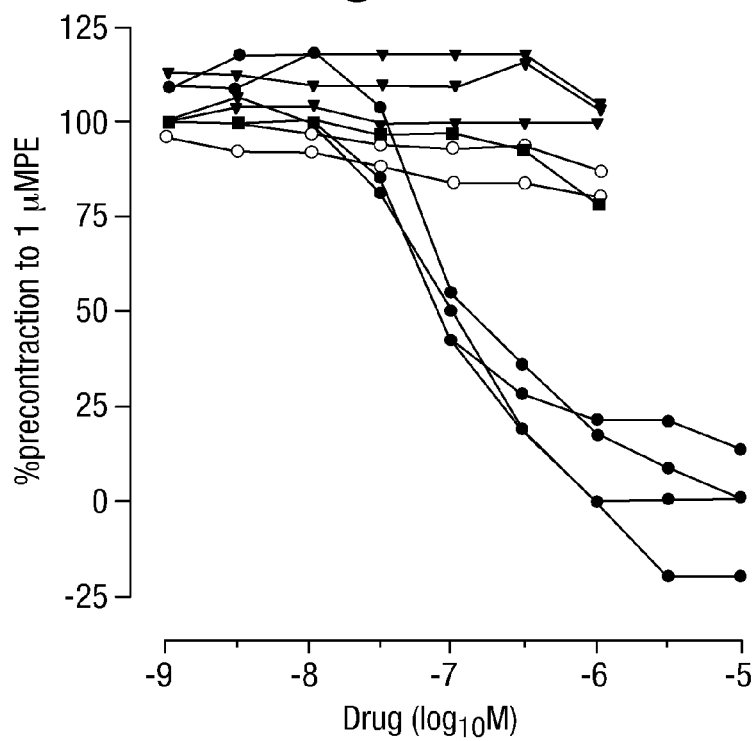
FIG. 5 shows the effect of $EP_2$ receptor antagonists on the relaxant response of cerebral blood vessels.

The above results indicate that the high relaxant potency of $PGE_2$ in small diameter cerebral arteries is indicative of the involvement of an EP receptor. Such inhibitory effects are invariably associated with either the $EP_2$ or the $EP_4$ receptor isoforms (Coleman, Smith & Narumiya, 1994, ibid). The EP isoform mediating this effect was determined by receptor exclusion studies using antagonists and agonists selective for other members of the prostanoid receptor family. Butaprost and AH13205 (trans-2-(4-[1-hydroxyhexyl]phenyl)-5-oxo-cyclopentaneheptanoate) are recognised as selective $EP_2$ agonists and thus their effect on human cerebral artery rings contracted with phenylephrine (1 μM) was determined. The results are shown in FIG. 5, which shows the cumulative concentration-effect curves to $PGE_2$ (closed circles), AH13205 (open circles) and butaprost (closed triangles). GR32191 (1 μM) was present in the bathing solution to block prostanoid $TP$-receptors.

It can be seen from FIG. 5 that neither compound caused relaxation of human cerebral arteries pre-contracted with phenylephrine (FIG. 5), excluding $EP_2$ receptor involvement in the relaxant response to $PGE_2$. These data provide support that the $PGE_2$ effect seen in this tissue is mediated via an $EP_4$ receptor or alternatively, a novel EP receptor(s) yet to be identified. The $EP_4$ receptor is proposed to be located on the vascular smooth muscle since in a number of experiments removal of the endothelium did not affect the relaxant response to $PGE_2$.

Effect of the $EP_4$ Receptor Antagonist, AH23848.

Figure 6:
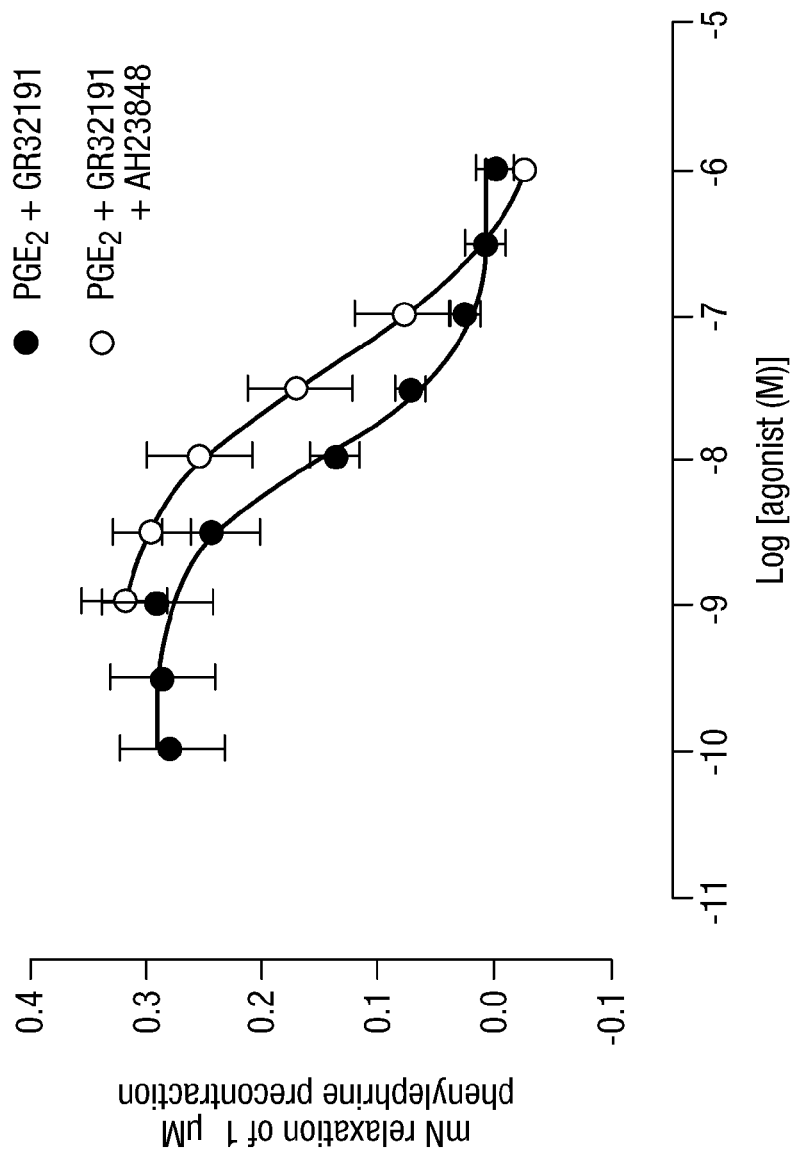
FIG. 6 shows the role of $EP_4$ receptors in $PGE_2$-mediated relaxation of cerebral arteries in the presence of a receptor antagonist.

The role of the $EP_4$ receptor in PGE2-mediated relaxation of phenylephrine pre-contracted middle cerebral rings was demonstrated using the putative $EP_4$ receptor antagonist AH23848. As a control, cerebral rings were pre-contracted with 1 mM phenylephrine, and concentration-dependently relaxed with PGE2 in the presence of 1 mM GR32191. Representative mean±s.e.m data of 4 middle cerebral artery rings from one donor are shown in FIG. 6, closed circles. To test the effect of the $EP_4$ receptor antagonist AH23848, cerebral rings were preincubated for 45 mins with 10 mM AH23848. AH23848 caused a significant rightward shift (P=0.004, 2 tailed T-Test) in the PGE2-mediated relaxation (Log EC50 (M) PGE2 7.87±0.07; PGE2+10 mM AH23848 −7.19±0.09)—FIG. 6, open circles.

Effect of $PGE_2$ on Coronary and Pulmonary Arteries.

It has also been found that $PGE_2$ failed to cause relaxation of coronary artery and pulmonary artery which had been precontracted with submaximal concentrations of U46619 or phenylephrine. Rings (2-4 mm internal diameter) were prepared from sections of pulmonary or coronary artery (n=3 each). They were mounted in organ baths under isometric conditions, in gassed Krebs solution (containing indomethacin) at 37° C., and 1-1.5 g initial tone.

After at least 60 min equilibration, tone was induced with U-46619 (10-100 nM) in pulmonary artery or either phenylephrine (1-10 μM) or endothelin-1 (−7M) in coronary artery. After a stable plateau had been obtained, tissues received a cumulative concentration effect curve to $PGE_2$, at log dose intervals, with at least 3 minutes at each concentration. After a maximum response had been obtained, all tissues were treated with cicaprost (0.1-1 μM), to induce relaxation.

Figure 7A:
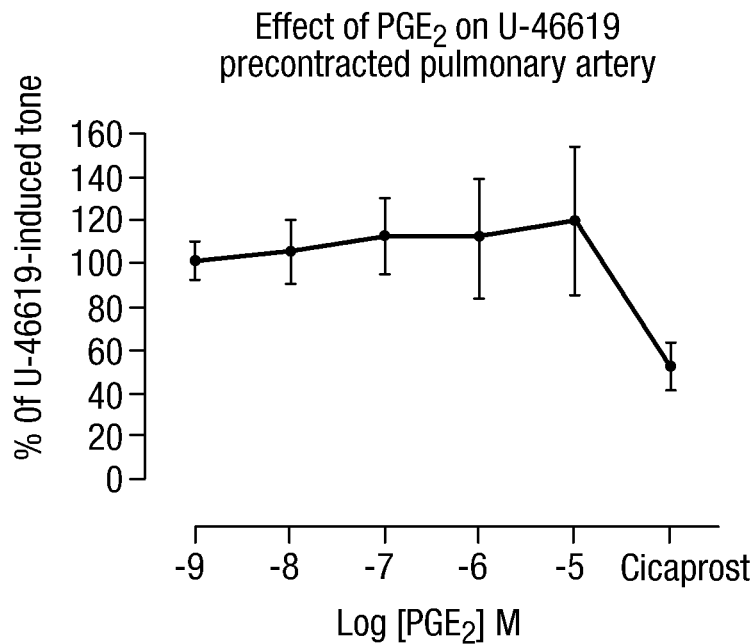
FIG. 7 shows the effect of $PGE_2$ on pre-contracted preparations of pulmonary (FIG. 7A) or coronary (FIG. 7B) artery.
Figure 7B:
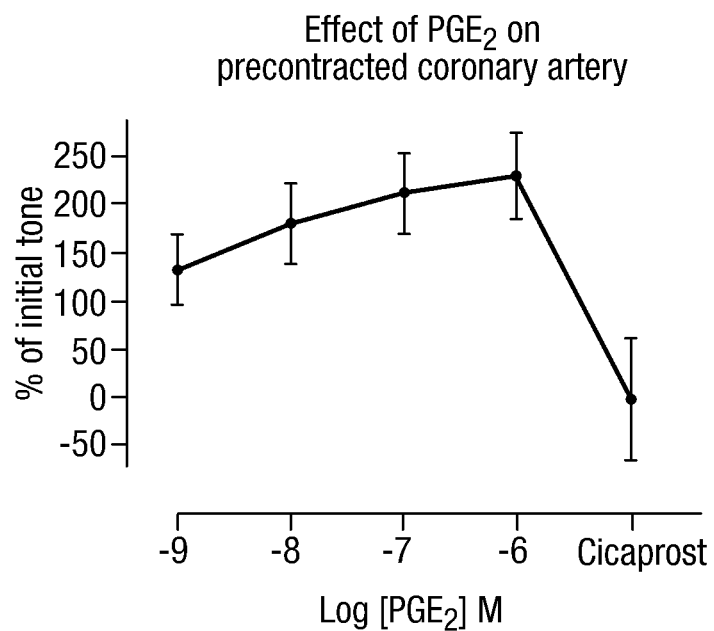

Application of U-46619 (pulmonary artery, see FIG. 7A) or phenylephrine or endothelin-1 (coronary artery, see FIG. 7B) induced significant increases in basal tone in all preparations. After a stable response had been obtained, application of $PGE_2$ did not cause relaxation in any preparation, in either coronary or pulmonary artery. The data of FIG. 7 are shown as mean±s.e. mean for n=3 donors.

Thus application of $PGE_2$ failed to induce relaxation of either pulmonary or coronary artery preparations. A small contraction was induced by $PGE_2$ in coronary artery, which is likely to be due to the activation of $EP_3$ receptors. Application of cicaprost induced a relaxation in all preparations, indicating that the tissues were viable and able to exhibit relaxatory responses. No evidence of inhibitory EP receptors could be found.

Thus assays of the invention which are configured to select an $EP_4$ receptor antagonist which is selective with respect to $EP_3$ receptors are of particular interest.

We claim:

1. A method for identifying an $EP_4$ receptor antagonist, which antagonist inhibits prostaglandin-induced relaxation of cerebral blood vessels having a diameter of less than 1 mm by selectively preventing the relaxation of cerebral vessels of less than 1 mm diameter, wherein said method comprises:
    (a) providing an $EP_4$ receptor together with at least one other receptor selected from the group of $EP_1$, $EP_2$ and $EP_3$ receptors;
    (b) bringing a potential antagonist into contact with said receptors;
    (c) determining whether said potential antagonist is an $EP_4$ receptor antagonist having a binding affinity for the $EP_4$ receptor at least 10-fold higher than for said $EP_1$, $EP_2$ and/or $EP_3$ receptors; and
    (d) selecting the $EP_4$ receptor antagonist which so binds as an agent for the treatment of primary headache disorder or drug-induced headache;
    wherein said $EP_4$ receptor is provided in the form of isolated vasculature from a cerebral artery.

2. The method of claim 1 wherein said other receptor is an $EP_3$ receptor.

3. The method of claim 1 which further comprises one or more of the following steps:
    (e') testing the $EP_4$ receptor antagonist so selected for safety and/or toxicity in a human or animal subject;
    (e'') testing the $EP_4$ receptor antagonist so selected in a human patient for efficacy in treating a primary headache disorder; and
    (e''') formulating the $EP_4$ receptor antagonist with one or more carriers, diluents or second agents for the treatment of primary headache disorders.

4. The method of claim 1 wherein step (c) comprises determining whether said potential antagonist is an $EP_4$ receptor antagonist having a binding affinity for the $EP_4$ receptor at least 10-fold higher than for said $EP_1$, $EP_2$ and $EP_3$ receptors.

5. The method of claim 4 which further comprises one or more of the following steps:
    (e') testing the $EP_4$ receptor antagonist so selected for safety and/or toxicity in a human or animal subject;
    (e'') testing the $EP_4$ receptor antagonist so selected in a human patient for efficacy in treating a primary headache disorder; and
    (e''') formulating the $EP_4$ receptor antagonist with one or more carriers, diluents or second agents for the treatment of primary headache disorders.

6. A method for identifying an $EP_4$ receptor antagonist, which antagonist inhibits prostaglandin induced relaxation of cerebral blood vessels having a diameter of less than 1 mm by selectively preventing the relaxation of cerebral vessels of less than 1 mm diameter, wherein said method comprises:
    (a) providing an $EP_4$ receptor in the form of isolated vasculature from a cerebral artery;
    (b) bringing a potential antagonist into contact with said receptor;
    (c) determining whether said potential antagonist is an $EP_4$ receptor antagonist which binds the $EP_4$ receptor; and
    (d) selecting the $EP_4$ receptor antagonist which so binds as an agent for the treatment of primary headache disorder or drug-induced headache.

7. The method of claim 6 wherein step (c) comprises determining whether the potential antagonist is an $EP_4$ receptor antagonist having a binding affinity for the $EP_4$ receptor at least 10-fold higher than for said $EP_1$, $EP_2$ and/or $EP_3$ receptors.

8. The method of claim 6 which further comprises one or more of the following steps:
- (e') testing the $EP_4$ receptor antagonist so selected for safety and/or toxicity in a human or animal subject;
- (e'') testing the $EP_4$ receptor antagonist so selected in a human patient for efficacy in treating a primary headache disorder; and
- (e''') formulating the $EP_4$ receptor antagonist with one or more carriers, diluents or second agents for the treatment of primary headache disorders.

* * * * *